United States Patent [19]

Basile et al.

[11] Patent Number: 4,502,611
[45] Date of Patent: Mar. 5, 1985

[54] AMALGAM DISPENSING DEVICE

[75] Inventors: Peter A. Basile, Hudson, Ohio; William J. Blatherwick, Hamilton Square, N.J.

[73] Assignee: Johnson & Johnson Dental Products Company, East Windsor, N.J.

[21] Appl. No.: 464,794

[22] Filed: Feb. 7, 1983

[51] Int. Cl.³ .............................................. G01F 11/16
[52] U.S. Cl. ........................................ 221/93; 221/96; 221/264; 222/192; 222/306; 222/361; 222/484
[58] Field of Search ........................ 222/192, 361, 484; 221/96, 264, 93

[56] References Cited

U.S. PATENT DOCUMENTS

| 1,553,113 | 9/1925 | Rutt | 221/484 |
| 2,065,785 | 12/1936 | Anschicks | 222/484 X |
| 3,168,213 | 2/1965 | DeGon | 221/96 |
| 3,467,277 | 9/1969 | Tolliver | 221/264 |
| 3,521,793 | 7/1970 | McShirley | 222/361 X |
| 4,139,030 | 2/1979 | Schroeder | 221/96 X |

FOREIGN PATENT DOCUMENTS

| 530102 | 9/1921 | France | 222/361 |
| 25828 | 2/1928 | France | 222/484 |

Primary Examiner—Joseph J. Rolla
Assistant Examiner—Frederick R. Handren
Attorney, Agent, or Firm—Charles J. Metz

[57] ABSTRACT

A device for storing and dispensing mercury and tablets comprising:
(a) a housing having a main discharge port;
(b) a normally closed mercury reservoir extending from the housing, the reservoir including a discharge port;
(c) a tablet container extending from the housing, the container having a discharge port;
(d) a passageway within the housing, part being below the mercury discharge port and another being above the main discharge port, the passageway being adapted to receive a slidable member, the slidable member being adapted to slide within the passageway between first and second positions;
(e) a vent including a passage communicating with the interior of the mercury reservoir near the top and with the passageway when the slidable member is not in the first position, but is sealed from the passageway when the slidable member is in the first position;
(f) a mercury metering cavity within the slidable member to receive mercury from the reservoir through the discharge port when the slidable member is in one of the two positions, and to discharge mercury through the main discharge port when it is in the other position; and
(g) a tablet dispenser in the housing, and being connected with the slidable member to slide in concert therewith, the tablet dispenser being adapted to slide between a first and second position and to receive a tablet from the tablet container when it is at one of the two positions and to discharge the tablet into the main discharge port when it is in the other of the two positions.

7 Claims, 10 Drawing Figures

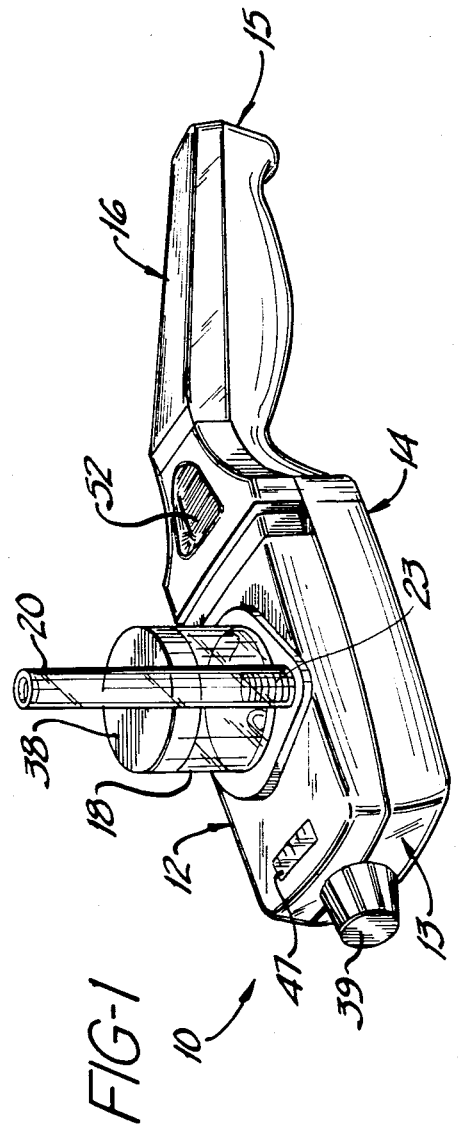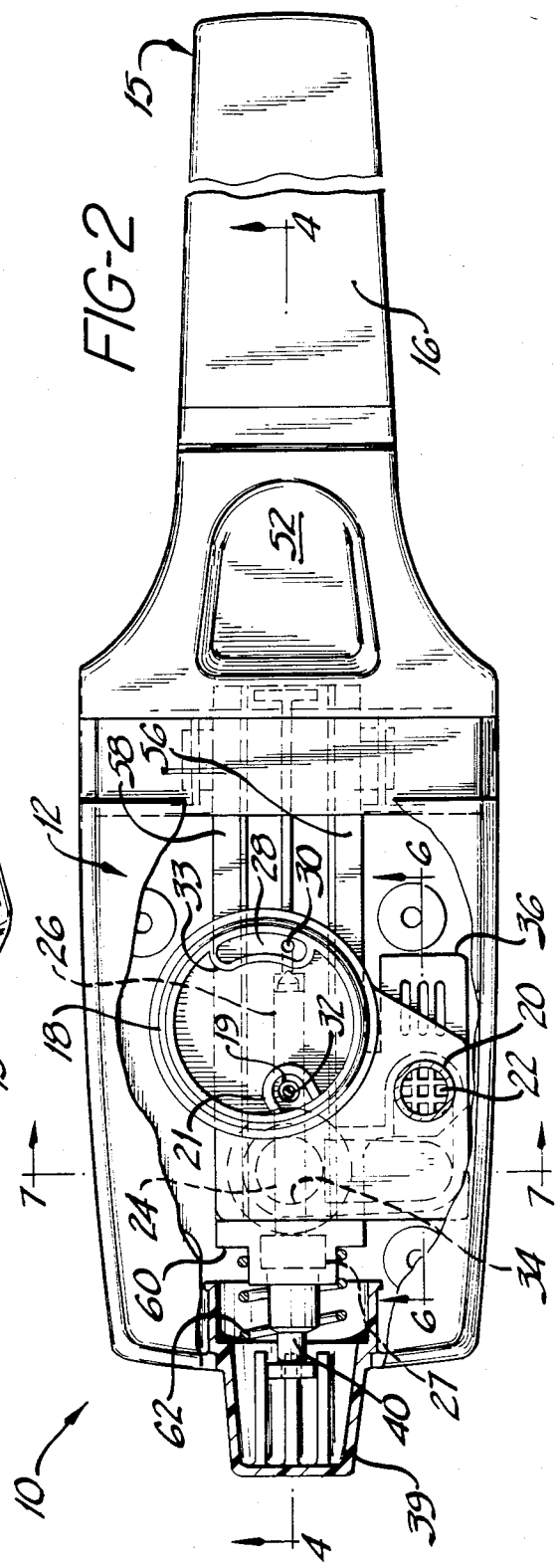
FIG-1
FIG-2

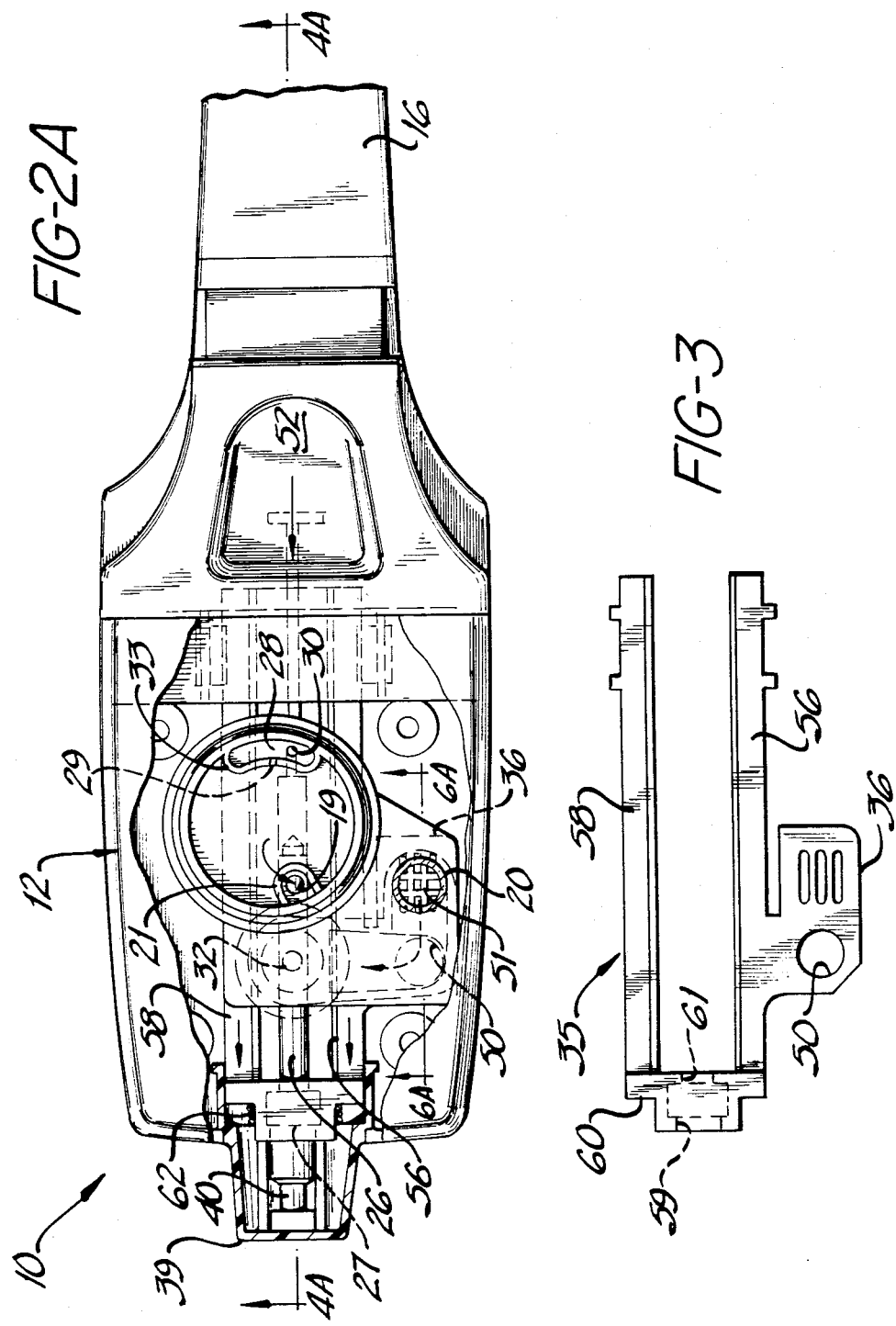

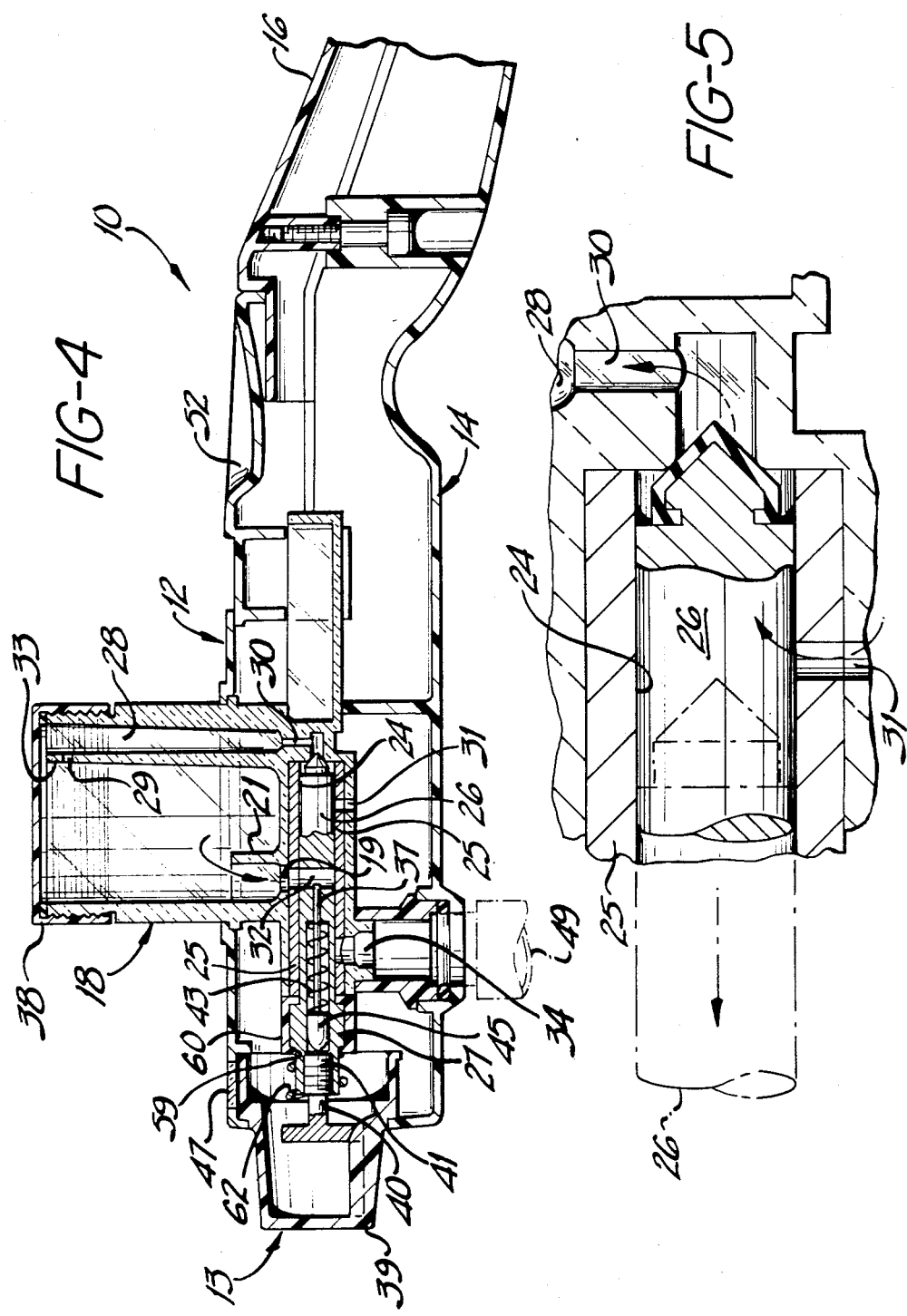

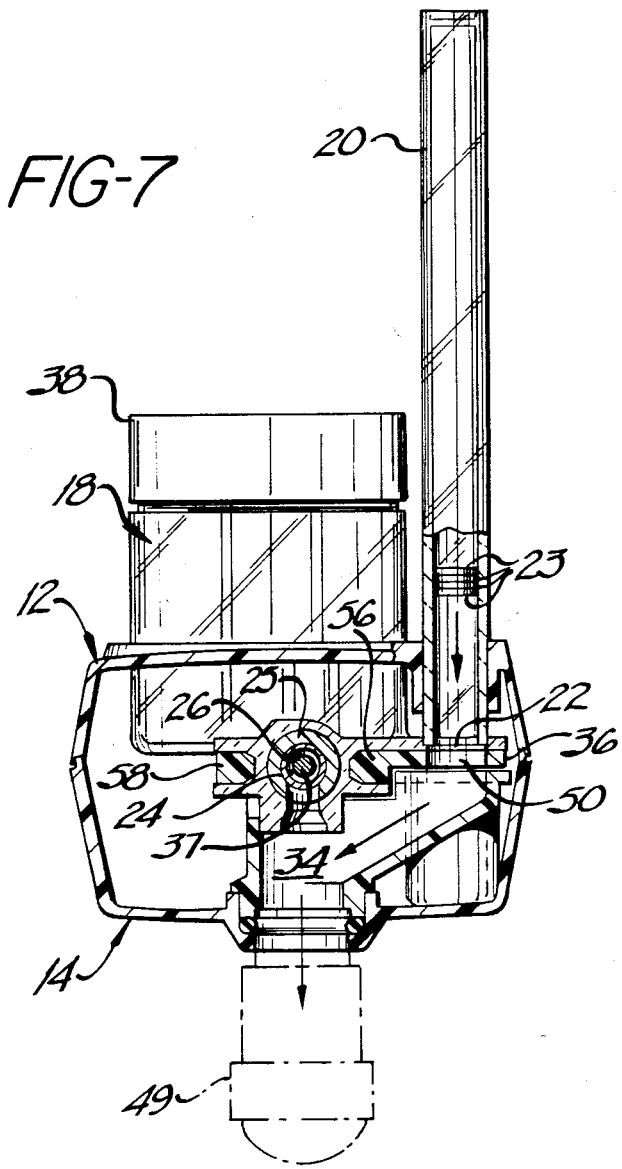

AMALGAM DISPENSING DEVICE

The invention relates to a device for storing and for dispensing metered amounts of mercury and amalgamable metal in tablet form.

BACKGROUND OF THE INVENTION

In the dental profession, silver amalgams are widely used for restorations on the biting surfaces of molars. The amalgam is prepared by the dentist by mixing a predetermined, carefully controlled volume of mercury with silver powder in the form of a tablet or pellet. One means of providing the mercury and silver alloy to the dentist is to provide a volume of mercury along with a supply of individual silver alloy tablets. The dentist then carefully measures the requisite amount of mercury and adds it to a mixing device with the silver alloy tablet, and then amalgamates or triturates the mercury/tablet mixture.

This invention relates to a device for storing a supply of mercury and silver alloy tablets, and for dispensing a single tablet with a predetermined, carefully metered amount of mercury.

SUMMARY OF THE INVENTION

The invention provides a device for storing and dispensing metered amounts of mercury and amalgamable metal in tablet form, which comprises:

(a) an elongated housing having an upper portion and a lower portion containing a main discharge port;

(b) a normally closed mercury reservoir extending upwardly from said upper portion, said reservoir including a mercury discharge port at the bottom thereof;

(c) a tablet container extending upwardly from said upper portion, said container containing a tablet discharge port at the bottom thereof;

(d) an elongated passageway disposed longitudinally within said housing, a portion of said passageway being directly below said mercury discharge port and another portion of said passageway being directly above said main discharge port, said passageway being adapted to receive a snugly fitting slidable member therein, said slidable member being adapted to slide within said passageway between a first, normally closed position and a second position;

(e) venting means including a vent passage communicating at one end directly with the interior of the mercury reservoir near the top thereof, and at the other end with said elongated passageway when said slidable member is in a position other than said first position, but wherein said vent passage is sealed from said elongated passageway when said slidable member is in said first position;

(f) a mercury metering cavity having a predetermined volume within said slidable member adapted to receive mercury from said mercury reservoir through said mercury discharge port when said slidable member is in one of said two positions, and to discharge mercury through said main discharge port when said slidable member is in the other of said two positions; and (g) slidable tablet discharge means located in said housing beneath said tablet container, said tablet discharge means being operatively connected with said slidable member to slide in concert therewith, said tablet discharge means being adapted to slide between a first position and a second position, and being adapted to receive a single tablet from said tablet container when the tablet discharge means is at one of said two positions and to discharge said single tablet into said main discharge port when said tablet discharge means is in the other of said two positions, whereby said mercury reservoir is closed to the atmosphere when said slidable member is in said first position and said mercury reservoir is vented by admission of air to the upper portion of the interior of the mercury reservoir when said slidable member is moved away from said first position, and whereby when said slidable member is moved from said first position to said second position and back again, a predetermined volume of mercury and one tablet are discharged from said main discharge port.

THE PRIOR ART

Biondo, in U.S. Pat. No. 4,023,715, discloses a mercury dispenser utilizing a slidable cam member to regulate the volume of mercury in the metering chamber. Biondo is stated to be an improvement on Krivig, U.S. Pat. No. 2,081,544, which discloses a screw-threaded rod slidable axially to vary the volume of the mercury metering cavity. Neither of these patents addresses the question of venting of the mercury storage chamber to the atmosphere.

McShirley, in U.S. Pat. No. 3,521,793, and Schroeder et al., in U.S. Pat. No. 4,139,030, both disclose mercury storage and dispensing devices having mercury storage chambers that are normally sealed from the atmosphere. However, in order to assure mercury metering accuracy, some means must be provided to permit air to enter the mercury storage chamber to make up for dispensed mercury. McShirley states that his device must be inverted to allow the pressure in the mercury storage chamber to be equalized (Col. 7, lines 8-11). Schroeder et al. use the mercury dispensing device of the above-cited Biondo patent. This device is also inverted to permit make-up air to enter the mercury storage chamber to equalize the pressure (see Col. 3 lines 42-55 of Biondo).

This invention provides a mercury and silver alloy storage and dispensing device having a normally sealed mercury storage chamber which automatically vents each time mercury is dispensed. In preferred aspects of the invention, the mercury metering cavity is designed to maximize mercury metering accuracy, and the apparatus is designed to minimize wear of moving parts so as to maintain this accuracy.

BRIEF SUMMARY OF THE DRAWINGS

FIG. 1 is a perspective view of a dispenser embodying the principles of the invention;

FIG. 2 is a top plan view, partially cut away, of the dispenser of FIG. 1, showing the various parts in the normally closed position;

FIG. 2A is a view similar to FIG. 2, showing the various parts in the discharge position;

FIG. 3 is a top plan view of the slide plate, including the tablet discharge plate, slide rods, and coupling plate;

FIG. 4 is a cross-sectional view taken along line 4—4 of FIG. 2;

FIG. 5 is an enlarged view of a portion of FIG. 4, showing the venting seal;

FIG. 7 is a transverse sectional view taken along line 7—7 of FIG. 2.

DETAILED DESCRIPTION OF THE INVENTION

Figure 4A:
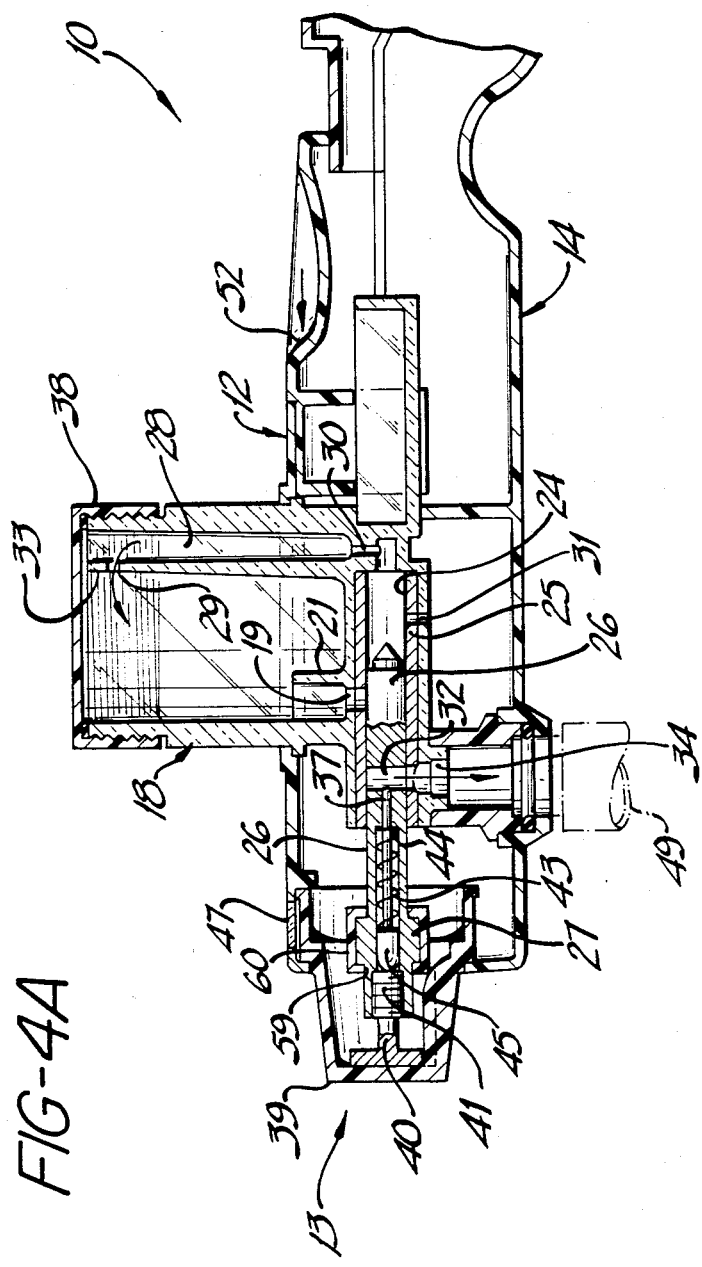
FIG. 4A is a cross-sectional view taken along line 4A—4A of FIG. 2A.

Referring first to FIG. 1, one embodiment of the invention is shown. The device 10 comprises an elongated housing having an upper portion 12, a lower portion 14 containing a main discharge port 34 (shown, e.g., in FIG. 4), a front end 13, a rear end 15, and a handle portion 16.

A closed mercury reservoir 18 is affixed to the upper portion 12 of the housing. The reservoir 18 includes a mercury discharge port 19 at the bottom (see FIGS. 2 and 4). In a preferred embodiment, the mercury discharge port 19 is surrounded by a slightly raised wall 21 (see FIG. 4), to discourage any solid impurities that may collect on the surface of the mercury from discharging through the mercury discharge port 19.

Figure 6:
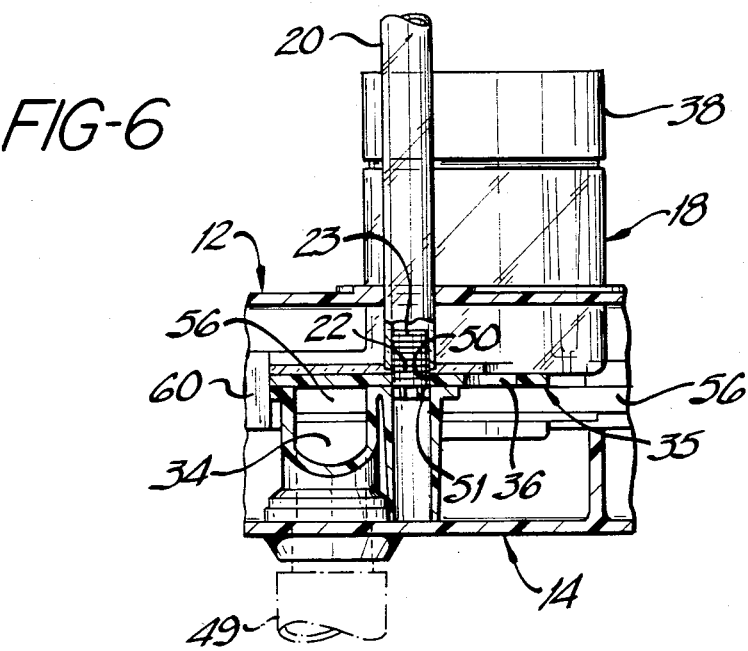
FIG. 6 is a cross-sectional view taken along line 6—6 of FIG. 2.

The device also contains a cylindrical tablet container 20 containing a supply of amalgamable silver alloy tablets 23. A tablet discharge port 22 (see FIGS. 6 and 7) is located at the bottom of the tablet container 20.

An elongated passage 24, best seen in FIGS. 4 and 4A, is disposed longitudinally within the housing. This passageway 24 is described by a metallic sleeve 25. The sleeve 25 is adapted to receive a snugly fitting slidable member 26 therein.

The slidable member 26 is normally in the closed position that is shown in FIGS. 4 and 5. While in the closed position, in the preferred embodiment a mercury metering cavity 32 that is hollowed out of the slidable member 26 is positioned directly below the mercury discharge port 19 to receive a charge of mercury equal to the volume of the said metering cavity 32.

An important aspect of the invention is the venting means that enables the mercury reservoir 18 to be vented each time mercury is dispensed, but which keeps the reservoir 18 sealed during normal storage. The venting means includes a vent passage 28 that communicates at the top end directly with the interior of the mercury reservoir, as through a small hole 29 (see FIGS. 4 and 4A) extending through the wall of the vent 28 into the interior of the reservoir 18 near the top thereof. In an alternative embodiment (not shown), instead of using the small hole 29, the wall 33 of the vent passage 28 can be slightly shorter than is needed to form a seal with the inside surface of the cap 38 on the mercury reservoir 18. At the other end of the vent passage 28, the vent communicates with the elongated passageway 24 through the vent port 30, but only when the slidable member 26 is moved away from the closed position that is shown in FIGS. 4 and 5. Thus, as is shown in FIG. 4A and in dashed lines in FIG. 5, when the slidable member 26 is moved away from the closed position, make-up air can pass through an air vent 31 into the passageway 24 and up into the reservoir 18 through the vent passage 28. (The air vent 31 communicates with the interior of the dispenser body, which is not sealed.) However, when the slidable member 26 is moved back to the closed position (as is shown in FIG. 4), the vent passage 28 is sealed from the surrounding atmosphere, to thereby deter mercury vapors from passing into the atmosphere and atmospheric contaminants from passing into the mercury reservoir 18.

Referring again to the mercury metering cavity 32 which is machined out of the slidable member 26 (see, especially, FIGS. 4 and 4A), the volume of this cavity 32 can be adjusted by a movable plunger 37 that is constructed and adapted to move in and out of the cavity by turning the adjustment knob 39. The adjustment knob 39 is coupled to a threaded adjusting screw 40 which passes through a threaded shaft 41, and engages the plunger 37. By moving the screw 40 in and out, the plunger 37 is moved in and out of the cavity 32, to thereby adjust the volume of said cavity 32. The plunger 37 is urged outwardly (that is away from the cavity 32) by a compression spring 43 that engages a shoulder 44 inside the slidable member 26 and a plunger button 45 at the front end of the plunger 37. Thus, when the screw 40 is turned to move inwardly toward the mercury metering cavity 32, the plunger 37 is forced against the compression spring 43 and will therefore move inwardly. However, when the screw 40 is turned so that it moves outwardly away from the cavity 32, then the compression spring 43 will move the plunger 37 outwardly to thereby withdraw the tip of the plunger 37 from the cavity 32. Preferably, the mercury metering cavity 32 is generally cylindrical in shape, in order to minimize surface area and hence the effects of surface tension on the metering of mercury.

When the mercury is dispensed from the cavity 32, excess surface tension energy can cause the formation of small droplets, which can deposit in the dispenser, for instance on the walls of the main discharge port 34, and thereby adversely affect the metering accuracy of the dispenser 10. The most preferred configuration of the mercury metering cavity 32 is a cylinder whose diameter is approximately equal to its height. (Theoretically, a sphere would be the best shape for the mercury metering cavity 32 since it would provide the lowest possible ratio of surface area to enclosed volume. However, it would be impractically expensive to produce a spherical cavity. Within the constraints of economic practicality for this type of device, a cylinder whose diameter equals its height is the next best shape to a sphere for minimizing surface area.)

If desired, a transparent window 47 can be provided on the upper portion 12 of the housing to view a graduated scale on the portion of the adjustment knob 39 that is postioned inside the upper portion 12 of the housing, to facilitate the adjustment of the position of the plunger 37.

In the preferred mode of operation, the metering cavity 32 is located directly beneath the mercury discharge port 19 when the slidable member 26 is in the closed position shown in FIG. 4. When the slidable member 26 is moved from the position shown in FIG. 4 to the position shown in FIG. 4A, then the mercury will discharge from the cavity 32 out of the main discharge port 34. Conveniently, the main discharge port 34 can be constructed so as to receive the open end of a triturating or mixing capsule 49, as is shown in FIGS. 4, 4A, 6, 6A, and 7. Therefore, material exiting from the main discharge port 34 will fall directly into the capsule 49.

Figure 6A:
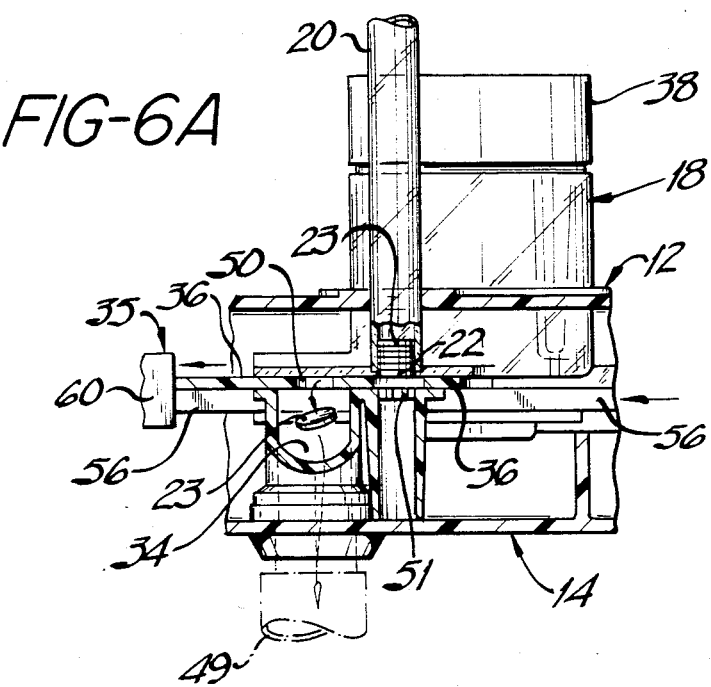
FIG. 6A is a cross-sectional view taken along line 6A—6A of FIG. 2A.

A slidable tablet discharge plate 36 (see FIGS. 2, 2A, and 3) containing a tablet cavity 50 sized to contain one tablet is located in a passage in the housing beneath the tablet container 20. The tablet discharge plate 36 is operatively connected with the slidable member 26 so that it will slide in concert therewith (this feature will be discussed more fully below). In the preferred embodiment of the invention, the tablet discharge plate 36 is constructed so as to receive a single tablet 23 from the tablet container 20 into the tablet cavity 50 when the slidable member 26 is in the normally closed position shown in FIGS. 2 and 6. Then, when both the slidable member 26 and the tablet discharge plate 36 are moved away from the closed position to the discharge position (shown in FIGS. 2A and 6A), a tablet 23 will fall out of the tablet cavity 50 into the main discharge port 34, as is shown in FIGS. 6A and 7. Conveniently, the passage in the housing in which the tablet discharge plate 36 slides can have a perforated bottom in the area under the tablet container 20 (as is shown in FIGS. 2 and 2A) so that tablet grit will fall out of the mechanism and will not promote wear and jamming of the slidable parts. The location of the perforated bottom is shown at 51 in FIG. 6A.

The slidable member 26 and the tablet discharge plate 36 are coupled to a slide button 52, that is arranged and constructed so as to be conveniently operated with the thumb. The tablet discharge plate 36 is part of a slide plate 35 (see FIG. 3) that includes slide rods 56, 58 and a coupling plate 60. The attachment of the slide button 52 to the slidable member 26 is preferably accomplished in a manner so as to reduce sideways forces on the slidable member 26, which will help to reduce jamming and uneven wear to thereby maintain both the seal of the reservoir 18 and the accuracy of the mercury metering. Thus, the slide button 52 is coupled directly to the two slide rods 56, 58, which extend through appropriate slots in the main housing to the coupling plate 60, located toward the front 13 of the device. The slidable member 26 is attached firmly to this coupling plate 60 by being force fit into a cavity 61 in the coupling plate 60. Thus, when the slide button 52 is pushed forward, it moves the slide plate 35 forward and thereby moves the tablet discharge plate 36 from the tablet receiving position (shown in FIG. 6) to the discharge position (shown in FIG. 6A), and it also concurrently moves the slidable member 26 forward from the mercury receiving position shown in FIG. 4 to the discharge position shown in FIG. 4A by transmitting the forward force through the two rods 56, 58 to the coupling plate 60, which then pulls the slidable member 26 forward towards the front end 13 of the device. The device is returned to its normally closed position by a compression spring 62 (seen FIGS. 2 and 2A) which presses against the coupling plate 60 from the interior of the adjustment knob 39.

The threaded shaft 41 through which the adjusting screw 40 passes is force fit into a second cavity 59 located in the front of the coupling plate 60.

What is claimed is:

1. A device for storing and dispensing metered amounts of mercury and amalgamable metal in tablet form, which comprises:
   (a) an elongated housing having an upper portion, a front end, and a lower portion containing a main discharge port;
   (b) a normally closed mercury reservoir extending upwardly from said upper portion, said reservoir including a mercury discharge port at the bottom thereof;
   (c) a tablet container extending upwardly from said upper portion, said container containing a tablet discharge port at the bottom thereof;
   (d) an elongated passageway disposed longitudinally within said housing, a portion of said passageway being directed below said mercury discharge port and another portion of said passageway being directly above said main discharge port, said passageway being adapted to receive a snugly fitting slidable member therein, said slidable member being adapted to slide within said passageway between a first, normally closed position and a second position;
   (e) venting means including a vent passage communicating at one end directly with the interior of the mercury reservoir near the top thereof, and at the other end with said elongated passageway when said slidable member is in a position other than said first position, but wherein said vent passage is sealed from said elongated passageway when said slidable member is in said first position;
   (f) a memory metering cavity having a predetermined volume within said slidable member adapted to receive from said mercury reservoir through said memory discharge port when said slidable member is in one of said two positions, and to discharge mercury through said main discharge port when said slidable member is in the other of said two positions; and
   (g) slidable tablet discharge means comprising plate containing a tablet receiving cavity and located in said housing beneath said tablet container, said tablet discharge means being operatively connected with said slidable member to slide in concert therewith, said tablet discharge means being adapted to slide between a first position and a second position, and being adapted to receive a single tablet from said tablet container when the tablet discharge means is at one of said two positions and to discharge said single tablet into said main discharge port when said tablet discharge means is in the other of said two positions, whereby said mercury reservoir is closed to the atmosphere when said slidable member is in said first position and said mercury reservoir is vented by admission of air to the upper portion of the interior of the mercury reservoir when said slidable member is moved away from said first position, and whereby when said slidable member is moved from said first position to said second position and back again, a predetermined volume of mercury and one tablet are discharged from said main discharge port, wherein said slidable member is moved by moving a slide button that is coupled to said slidable member by two parallel slidable rods that pass through said housing and which couple to said slidable member by coupling means located near the front end of said device.

2. The device of claim 1 wherein the mercury metering cavity is adjusted to receive a predetermined amount of mercury, and the slidable tablet discharge means is adjusted to receive a single tablet, when the slidable member is in said first position.

3. The device of claim 1 wherein said mercury metering cavity is generally cylindrical in shape.

4. The device of claim 1 wherein compression spring means return said slidable member from the discharge position to said first, normally closed position.

5. The device of claim 2 wherein the portion of the housing located directly beneath said tablet receiving cavity when the slidable member is in said first position, is perforated so as to permit tablet grit to fall out of said device.

6. The device of claim 1 wherein said mercury discharge port is surrounded by a raised wall.

7. The device of claim 3 wherein the shape of the mercury metering cavity is a cylinder whose diameter is approximately equal to its height.

* * * * *